(12) United States Patent
Glukhovsky et al.

(10) Patent No.: US 6,986,738 B2
(45) Date of Patent: Jan. 17, 2006

(54) SYSTEM AND METHOD FOR MANEUVERING A DEVICE IN VIVO

(75) Inventors: Arkady Glukhovsky, Nesher (IL); Mark G. Gilreath, Charlotte, NC (US); Gavriel Meron, Petach Tikva (IL); Yoram Ashery, Givat Shmuel (IL)

(73) Assignee: Given Imaging LTD, Yoqneam (IL)

( * ) Notice: Subject to any disclaimer, the term of this patent is extended or adjusted under 35 U.S.C. 154(b) by 157 days.

(21) Appl. No.: 10/212,139

(22) Filed: Aug. 6, 2002

(65) Prior Publication Data

US 2003/0120130 A1 Jun. 26, 2003

Related U.S. Application Data

(60) Provisional application No. 60/309,775, filed on Aug. 6, 2001.

(51) Int. Cl.
*A61B 1/00* (2006.01)

(52) U.S. Cl. ............................ 600/109; 600/114
(58) Field of Classification Search ................ 600/114, 600/109, 160, 407, 473, 476, 585; 348/65, 348/77
See application file for complete search history.

(56) References Cited

U.S. PATENT DOCUMENTS

| | | | |
|---|---|---|---|
| 4,198,960 A | 4/1980 | Utsugi | |
| 4,278,077 A | 7/1981 | Mizumoto | |
| 4,782,819 A | 11/1988 | Adair | |
| 4,819,620 A | 4/1989 | Okutsu | |
| 4,905,670 A | 3/1990 | Adair | |
| 5,026,368 A | 6/1991 | Adair | |
| 5,143,054 A | 9/1992 | Adair | |
| 5,381,784 A | 1/1995 | Adair | |
| 5,604,531 A | 2/1997 | Iddan et al. | |
| 5,653,677 A | 8/1997 | Okada et al. | |
| 6,240,312 B1 | 5/2001 | Alfano et al. | |
| 2002/0103417 A1 * | 8/2002 | Gazdzinski | 600/109 |

FOREIGN PATENT DOCUMENTS

| | | |
|---|---|---|
| JP | 2000342527 | 12/2000 |
| WO | WO 01/65995 | 9/2001 |

* cited by examiner

*Primary Examiner*—Beverly M. Flanagan
(74) *Attorney, Agent, or Firm*—Pearl, Cohen, Zedek, Latzer, LLP

(57) ABSTRACT

A system and method for maneuvering a device in vivo, wherein a tube has a longitudinal axis, a distal end and a proximal end, and an in vivo sensing device is changeably connected to the distal end of the tube. Typically, the sensing device may be moved from one position where it is, for example, within the axial profile of the tube or along the longitudinal axis of the tube, to a second position, where it is not.

36 Claims, 4 Drawing Sheets

SYSTEM AND METHOD FOR MANEUVERING A DEVICE IN VIVO

The present application claims the benefit of prior provisional application 60/309,775, entitled "A SYSTEM AND METHOD FOR MANEUVERING A DEVICE IN VIVO" and filed on Aug. 6, 2001.

FIELD OF THE INVENTION

The present invention relates to the field of in vivo diagnosis and/or therapeutics. More specifically, the present invention relates to a system and method for maneuvering a sensing device in vivo.

BACKGROUND OF THE INVENTION

In vivo tools are used in diagnosis and therapeutics of diverse body systems. In vivo sensing can enhance a practitioner's ability to safely and easily detect internal body features and occurrences with minimal intrusion. In vivo diagnostic and/or therapeutic processes (such as surgical procedures, biopsy or sampling procedures and delivering treatment to specific in vivo locations) may be enhanced due to the miniature sensors available today. Miniature sensors can be used for sensing in vivo conditions in body lumens, such as, temperature, pH or pressure. Also, image sensors are used for the visual inspection of body lumens or cavities. Medical procedures in body lumens and cavities, such as laparoscopic surgery procedures and gastroenterology procedures are typically performed by medical devices that are passed through trocars or endoscopes which usually comprise viewing or imaging means for simultaneously viewing and performing a procedure in vivo.

The endoscopes available today typically comprise an outer tube (which is inserted into the body) with an image sensor and viewing lens located at the distal tip of the tube, a plurality of light transmitting fibers for bringing illumination to a site of interest in the body lumen and channels inside the outer tube. The channels are utilized for air insertion, for insufflation of the body lumen, for water injection, for cleaning the viewing lens, for suction and for passing devices, such as forceps, stents, dissecting or tissue removal devices, catheters etc. The outer tube is connected to a control body which the physician holds and which may feature buttons and pulley wheels for activation and control of the endoscope and channel functions. An umbilical cable connects the control body to a light source and video processor.

The angle of view afforded by an image sensor or the accessibility of any other sensor that is located at the endoscope tip to remote or concealed portions of the body lumen are dependent on the maneuverability of the endoscope tip. Typically, the endoscope tip may have a limited range of movement so that a wide angle of view, for example, is usually achieved by specific design of the viewing lens or other optical elements at the endoscope tip.

Autonomous sensors may access portions of body lumens that are inaccessible to endoscopes, however autonomous devices are not easily controlled and many of the procedures that can be performed utilizing endoscopes can not be performed by such autonomous devices.

There is therefore a need for facilitated performance of in vivo procedures.

SUMMARY OF THE INVENTION

Embodiments of the present invention provide a system and method for maneuvering a sensing device in vivo. Certain embodiments may provide endoscopes and/or other in vivo diagnostic and/or therapeutic tools with a maneuverable sensing device, thereby facilitating the performance of in vivo procedures.

A system according to one embodiment of the invention comprises a tube having a distal end and a proximal end and an in vivo sensing device that may be changeably connected to the distal end of the tube. Typically, the distal end may be inserted into a body lumen while the proximal end may be accessible to an external operator. The tube may include channels for passing through them tools, water, air etc., as known, for example, in the field of endoscopy.

According to one embodiment of the invention the sensing device, which may be any suitable sensing device known in the art, may be connected to the distal end of the tube in at least two changeable modes. In at least one first mode the sensing device may be connected to the distal end of the tube to substantially form a continuum along the longitudinal axis of the tube. In at least one second mode the sensing device may be connected to the distal end of the tube so as not to form a continuum along the longitudinal axis of the tube. In one embodiment the sensing device in a second mode is connected to the distal end of the tube along side the tube essentially in parallel to the longitudinal axis of the tube.

According to some embodiments, the system may comprise mechanisms such as a track, ramp or retractable arm or spring for coupling or connecting the tube and sensing device and/or for effecting the change from a first mode to a second mode.

In one method according to an embodiment of the invention a device is inserted in vivo while the sensing device is connected to the distal end of the tube in a first mode. The tube is moved to a desired location, possibly being aided by the sensing device, at which point the sensing device's connection to the distal end of the tube is changed to a second mode.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

A system according to one embodiment of the invention may be used in a diagnostic and/or therapeutic procedure wherein a tube, which includes, for example, tools or working channels for, for example, inserting tools, is guided to a desired location in a body lumen aided by a sensing device positioned at the distal end of the tube and connected so as to substantially form a continuum along the longitudinal axis of the tube. At a desired location the sensing device's connection to the distal end of the tube is changed to a second mode in which, for example, the sensing device is positioned alongside the tube, not forming a continuum along the longitudinal axis of the tube. In the first mode the distal end of the tube may be obstructed by the sensing device. However in the second mode the distal end of the tube is not obstructed by the sensing device and the tube may be used for inserting tools into the body lumen and/or for insufflation, etc., of the body lumen. Furthermore, in the second mode the sensing device may continue to assist in performing an in vivo procedure. Other procedures may be performed with the tube.

For example, in one embodiment of the invention the sensing device may be an imaging unit that may include an image sensor, an optical system, an illumination source and possibly a transmitter for transmitting image data to a receiving unit. In this embodiment, the imaging unit in a first mode assists in guiding the tube to a desired location, while not obstructing the tube movement in the body lumen. In a second mode the imaging unit provides a view of the body lumen for an external operator to assist the operator in performing an in vivo procedure utilizing the tube and its working channels or tools.

In other embodiments the sensing device may not be precisely along the central longitudinal axis of the tube, and may be partially outside the profile of the tube. For example, if the profile or area of the sensing device is smaller than that of the tube, the sensing device may be off center when in its first position. Typically, the sensing device may be moved from one position where it is, for example, within the axial profile of the tube or along the longitudinal axis of the tube, to a second position, where it is not.

Figure 1A:
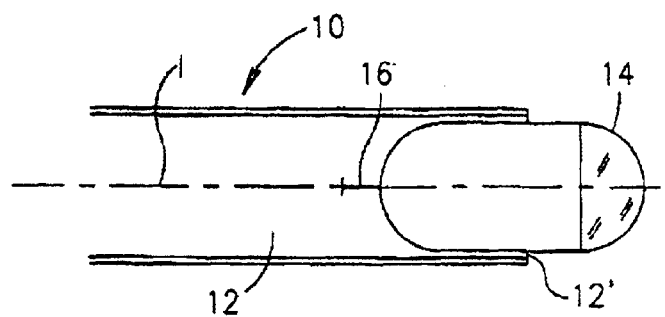
FIGS. 1A and 1B are schematic side view illustrations of a system according to an embodiment of the invention.
Figure 1B:
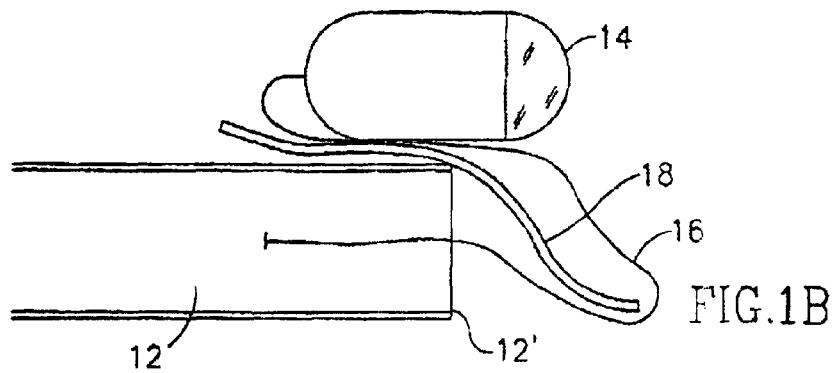

Reference is now made to FIGS. 1A and 1B in which an embodiment of the system of the invention is schematically illustrated. System 10 includes, for example, a tube 12 and a sensing device 14 that is connected to the tube 12 at the tube's distal end 12'. The tube 12 may be flexible or rigid as required. For example, a flexible endoscope is usually used for colonoscopic procedures and procedures in the upper part of the GI tract. The tube 12 may be designed and fabricated similarly to known catheters, endoscopes, needles, stents, laparascopes, rigid endoscopes and the like, in accordance with specific requirements.

The sensing device 14 may be any suitable in vivo sensing device. In one embodiment the sensing device 14 is an imaging unit for imaging the GI tract. Sensing device 14 may be similar to the imaging unit described in published International Application publication number WO 00/76391 entitled "An Optical System" and published on Dec. 21, 2000, which is assigned to the common assignee of the present invention and which is hereby incorporated by reference. In another embodiment the sensing device 14 may be a capsule shaped autonomous image sensor such as the devices described in U.S. Pat. No. 5,604,531 to Iddan or in International Application publication number WO 01/65995 entitled "A Device and System for in vivo Imaging" and published on Sep. 13, 2001, both of which are assigned to the common assignee of the present invention and which are incorporated by reference. Other sensing devices may be used.

The sensing device 14 may include, for example, an image sensor, such as a CCD or a CMOS image sensor, an optical system (which typically includes, for example, lenses and/or mirrors and/or prisms), an illumination source, such as LEDs and a transmitter (either wireless or wired) for transmitting image or other data to a receiving unit. Optionally, these elements of the sensing device 14 may all be wireless or transmit via radio waves and may be powered, for example, by a battery contained in sensing device 14 or may be powered through, for example, an electrical wire connection to the sensing device 14. The electrical wire may be used, inter alia, for wired transmission of image data. The sensing device may include sensors other than an image sensor.

In FIG. 1A the sensing device 14 is connected to the tube 12 through, for example, an elastic cord or wire 16 that is anchored to the tube 12 in proximity to the tube 12 distal end 12'. The wire 16 is relaxed and the sensing device 14 is attached to the tube 12 in a continuum along the longitudinal axis (I) of the tube 12. In the embodiment illustrated in FIG. 1B the sensing device 14 has been advanced along the tube 12 pulling the elastic wire 16 behind it. Once the sensing device 14 exits the tube 12 a ramp 18 is lowered in front of the tube 12 at distal end 12'. The ramp 18, which is connected to the tube at its distal end, pushes the elastic wire 16 forcing the sensing device 14 up the ramp 18, bringing it along side the tube 12, essentially parallel to the longitudinal axis of the tube 12. Optionally, the sensing device 14 may be fastened to the ramp 18 or to the tube 12 to secure its position. At this point the elastic wire 16 is taut and will pull the sensing device 14 back to its initial position in the tube 12 (the initial position is, for example, as shown in FIG. 1A), once the sensing device 14 is released from its position alongside the tube 12. The elastic wire 16 may also push ramp 18 to its raised position (not shown).

Alternatively, the ramp 18 may be actively raised thereby releasing the pressure on the elastic wire 16 enabling the elastic wire 16 to pull the sensing device 14 back to its initial position in the tube 12 (FIG. 1A). Lowering and raising the ramp 18 and/or controlling the advancement of the sensing device 14 through the tube 12 can be achieved by known methods. Springs and pulleys can be used by an external operator to control the ramp 18 and/or control the movement of the sensing device 14. Alternatively, passive mechanisms can be utilized to control the ramp 18 and/or control the movement of the sensing device 14. For example, the ramp 18 can be controlled by a latch made of, for example, a bi stable material or a shape memory polymer that is heated or cooled as required to enable the lowering of the ramp. Similarly, the advancement of the sensing device 14 through the tube 12 can be controlled by a spring of bi stable material or a shape memory polymer. Other materials can be used. The ramp may be of other configurations.

The wire 16 may not be elastic, but instead may be moveable via a control. In one embodiment the device 14 may exit the tube 12 on the action of a control such as a wire (not shown) pulling the device 14 from the outside of the tube 12.

In one embodiment, the ramp is formed as part of or extends from one lip of distal end 12' of the tube 12. When the device 14 exits the tube (for example, if the wire 16 is relaxed, or if another wire or control, not shown, pulls the device 14), the tube may, for example, slide up the outside portion of the ramp to be drawn away from the longitudinal axis to the tube 12.

Figure 2A:
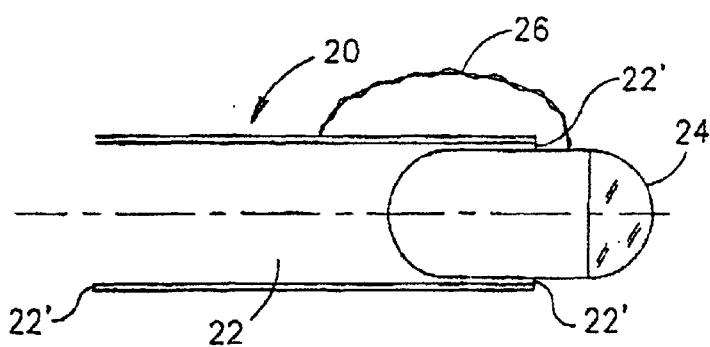
FIGS. 2A and 2B are schematic side view illustrations of a system according to another embodiment of the invention.
Figure 2B:
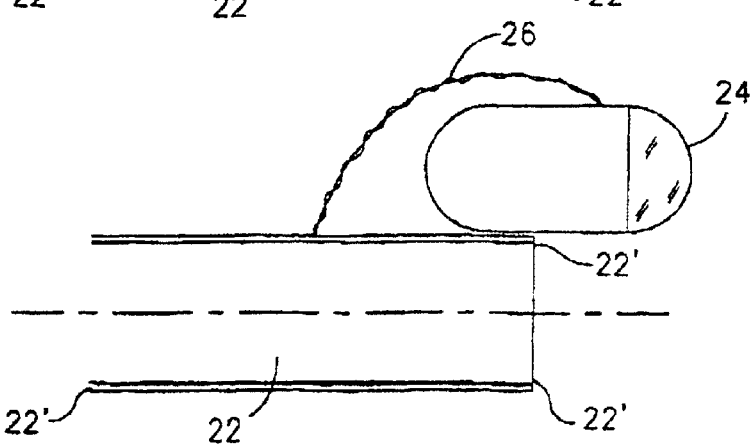

In an embodiment illustrated in FIGS. 2A and 2B a sensing device 24 is coupled to a tube 22 through a spring 26. Typically spring 26, or any other suitable retractable or non retractable arm, is connected to the tube 22 either on the tube external perimeter or in its internal diameter (for example, as illustrated in FIG. 1B). In a first mode, illustrated in FIG. 2A, for example, while the system 20 is being pushed through the abdomen or through the GI tract or other body lumen (such as a blood vessel), the sensing device 24 is secured to the tube 22 such that it forms a continuum with the tube 22 along the tube 22 longitudinal axis and such that spring 26 is stretched. This first mode enables easy passage of the system 20 through the body lumen.

In another mode, illustrated in FIG. 2B, the sensing device 24 is no longer secured to the tube 22. The spring 26 recoils pulling the sensing device 24 with it so that it is now positioned alongside the tube 22. This second mode is desirable, for example, when the system 20 is no longer moved through the body lumen (e.g., at a location where surgery or other procedures are to be performed).

The securing and releasing of the sensing device 24 from the tube 22 may be achieved by known methods, such as by using a degradable glue or by mechanically moving apart the distal tips 22' of the tube 22 to release their hold on the sensing device 24. Other methods may be used.

Figure 3A:
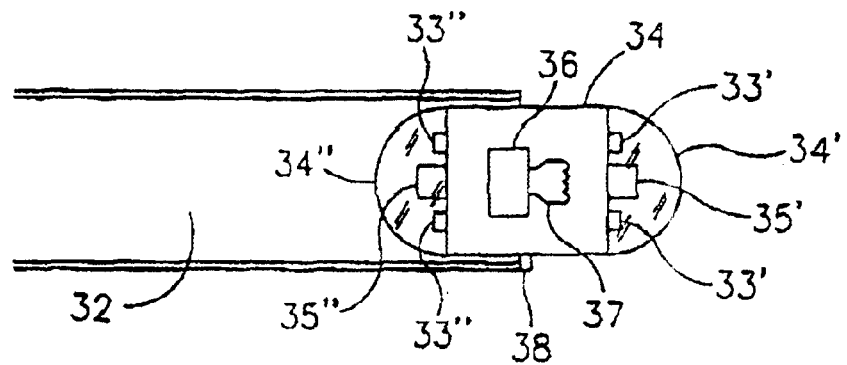
FIGS. 3A and 3B are schematic side view illustrations of a system according to yet another embodiment of the invention.
Figure 3B:
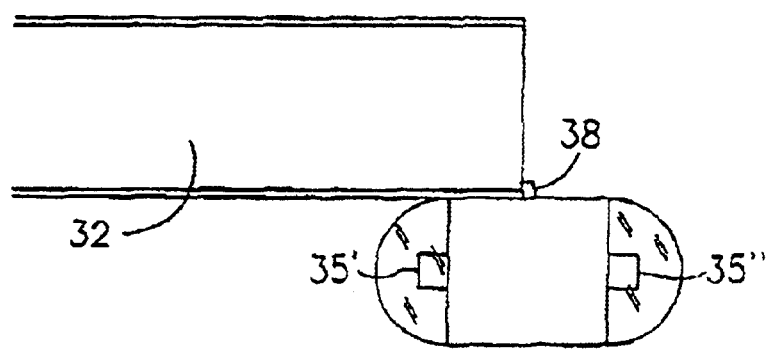

In the embodiment illustrated in FIGS. 3A and 3B an imaging unit 34 is changeably connected to a tube 32 through a hinge 38, or, optionally, as described above. The imaging unit 34 comprises two viewing ends 34' and 34" each including illumination sources 33' and 33" and two optical paths, respectively. (An optical path may be considered to be the course followed by light rays incident on an in vivo site and remitted from it onto an image sensor, such as a CMOS image sensor.) In the two optical paths remitted light is directed to image sensors 35' and 35" respectively. The imaging unit 34 further comprises a power source (not shown), which may provide power to the entirety of electrical elements of the imaging unit 34, and a transmitter 36 and antenna 37 for transmitting image signals from the image sensors 35' and 35". Optionally, the viewing ends 34' and 34" may comprise an optical window as described in the above mentioned WO 00/76391, or other structures. In one embodiment, multiple optical paths may be included, leading to or focusing on one imager.

In a first mode, illustrated for example in FIG. 3A, the imaging unit 34 is secured to the tube 32 such that it forms a continuum with the tube 32 along the tube 32 longitudinal axis. Images of the body lumen may be obtained by image sensor 35', while image sensor 35", and illumination sources 33" may be inactive.

In another mode, illustrated for example in FIG. 3B, the imaging unit 34 is no longer secured to the tube 32. The hinge 38 enables the advancement of the imaging unit 34 out of the tube 32. However, once the imaging unit 34 exits the tube 32 it is pulled down by gravity and hangs, along side the tube 32, or possibly at an essentially right angle to the tube 32, on hinge 38. The directionality of the imaging unit 34 is typically altered such that image sensor 35', which was initially forward viewing, is now viewing the rear or the side. In the second mode image sensor 35", which is now typically forward viewing, may be activated as well as illumination sources 33". In this second mode the imaging unit 34 may be capable of simultaneously obtaining images of a body lumen, for example, the GI tract, from two ends of the unit, thereby enabling a wide angle of view of the body lumen. Furthermore, the tube 32 is cleared and can be used, for example, for performing in vivo procedures (as will be discussed below). Imaging unit 34 may be displaced or moved by a method other than gravity, for example, a wire or control extending along the tube.

The two images (typically front and rear, although other configurations and perspectives may be used) obtained by image sensors 35" and 35' respectively, can be displayed separately or as a single combined image. In one embodiment a separate transmitter and channel of transmission may be assigned to each image sensor for simultaneous transmitting of signals from the body lumen. Alternatively, the output of several image sensors may be combined over a single transmitter (such as transmitter 36) and channel of transmission, e.g., by using different carrier frequencies. The combination of information from the different image sensors over the single channel may be done either by selecting a bit from a different image sensor each time, thus transmitting all the images almost simultaneously, or by transmitting image after image.

According to one embodiment the two images obtained by image sensors 35' and 35" may be combined into a single image prior to being transmitted to a receiving unit, for example, by applying an algorithm which assigns each image point (pixel) in the different images to another point (pixel) of the single combined image. However, since the operation of combining images into a single image may require significant processing effort and computing resources, this operation is usually performed off-line (after receiving the image transmitted from the image sensors) in an external recording/processing device. The separation of the images may be performed on line by known image processing methods or by adding tags to the different images, for example, adding a code for the image obtained by image sensor 35' and a different code for the image obtained by the image sensor 35". Other transmission methods may be used.

Figure 4A:
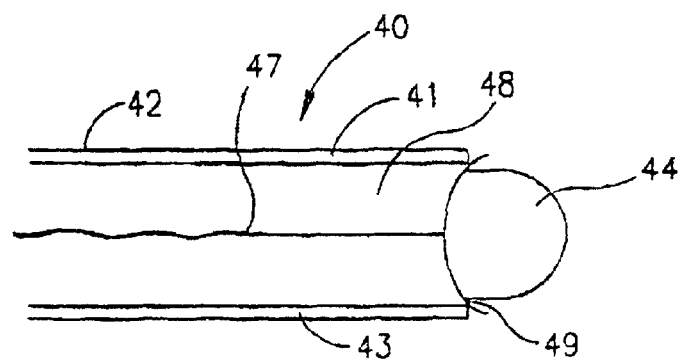
FIGS. 4A and 4B are schematic side view illustrations of a system according to a further embodiment of the invention.
Figure 4B:
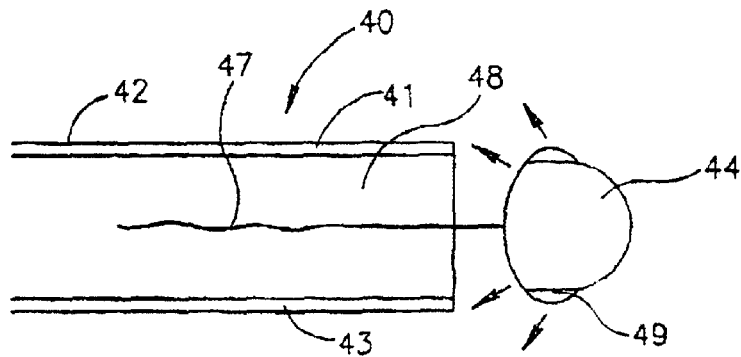

Another embodiment of the invention is schematically illustrated in FIGS. 4A and 4B. In this embodiment the system 40 includes, for example, a tube 42 having a channel 48, through which an arm 47 extends, and channels 41 and 43 for, for example, passing water and/or air and/or tools into the body lumen. At the distal end of the arm 47 there is a rotateable holding unit 49 for holding a sensor device 44. The arm 47 and the rotateable holding unit 49 can both be controlled by an external operator. Alternatively, the sensor device 44 may be directly and rotateably connected to the distal end of arm 47, eliminating the need for a holding unit 49. Other channels or arrangements of channels may be included, and not all channels used in the example need be included.

In a first mode, illustrated for example in FIG. 4A, the distal openings of channels 48, 41 and 43 may be blocked by the rotateable holding unit 49. The sensor device 44 forms a continuum with the tube 42 along the tube 42 longitudinal axis. In a second mode, illustrated for example in FIG. 4B, the arm 47 is pushed forward, for example, by an external operator, and the rotateable unit 49 and with it the sensor device 44, are moved away from the distal end of the tube 42, clearing the distal openings of the channels 48, 43 and 41. These channels can now be utilized for, for example, passing water/air and/or tools to the body lumen, for performing an in vivo procedure or another function. At the same time the rotateable unit 49 can be rotated (as indicated by the arrows in FIG. 4B) thus enabling the sensor device 44 accessibility to usually inaccessible parts of the body lumen. For example, a wide angle of view of a body lumen can be achieved by an image sensor that can be rotated as described.

Figure 5:
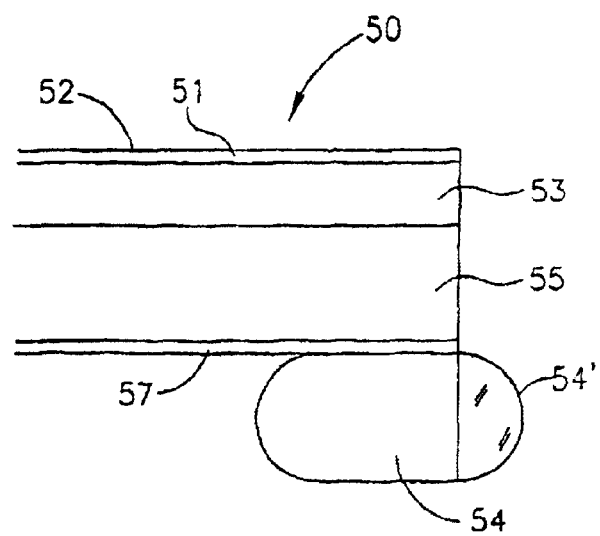
FIG. 5 is a schematic side view illustration of a system according to yet another further embodiment of the invention.

FIG. 5 is a more detailed schematic illustration of the tube of the system according to an embodiment of the invention. The system 50 includes, for example, a tube 52 and a sensor device 54. The sensor device 54 may be, for example, an imaging device having an optical window 54', as described above and the tube 52 may be, for example, an endoscope utilized in cases of, for example, internal gastric bleeding. Other sensing devices and tubes may be used.

The tube 52 includes, for example, a water/air channel 51 for flushing or insufflating the GI tract, as required; a tool channel 53 for passing a tool into the GI tract, such as a band ligation or cautery tool for stopping the internal bleeding; a suction channel 55 for clearing the contents of the GI tract; and a water jet channel 57 for cleaning the optical window 54'. The tube 52 can be connected at its proximal end to a control handle and be operated as known in the endoscope field. Other channels or arrangements of channels may be included, and not all channels used in the example need be included.

Various embodiments of the invention can be easily guided to an in vivo location, possibly aided by the sensor device of the system. When at an in vivo location the sensor device can be maneuvered away from the tube of the system, for example, as described in any of the above embodiments, enabling accessibility of the sensor device and economic use of the tube.

According to an embodiment of the invention there is provided a method for performing an in vivo procedure. In vivo procedures may include diagnostic procedures, such as imaging or sampling, or therapeutic procedures, such as ligating, etc. According to one embodiment a system such as exemplified above may be inserted in vivo while the sensing device is connected to the distal end of the tube in a first mode. The tube is moved to a desired location, possibly being aided by the sensing device, at which point the sensing device's connection to the distal end of the tube is changed to a second mode. Typically, when the sensing device's connection to the distal end of the tube is changed to the second mode, working channels in the tube may be utilized for, for example, irrigation, insufflation or surgery.

Figure 6:
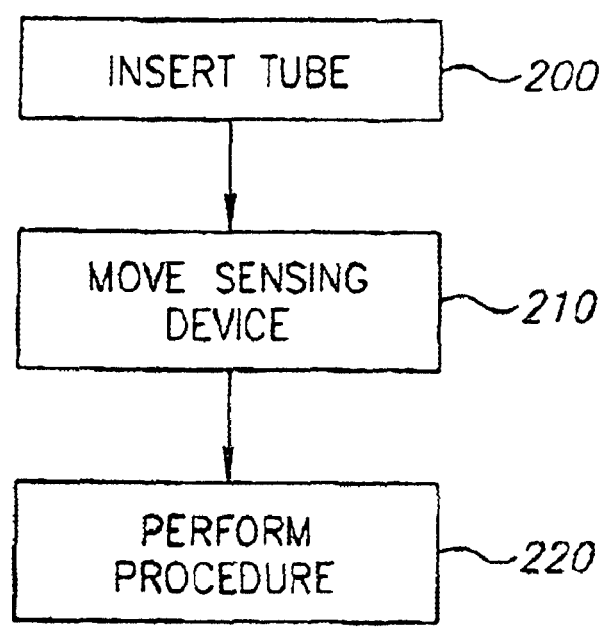
FIG. 6 depicts a series of steps according to one embodiment of the present invention.

FIG. 6 depicts a series of steps according to one embodiment of the present invention. Referring to FIG. 6, in step 200, a tube is inserted in-vivo. The tube may be, for example, an endoscope, or may be another type of tube. The tube includes a sensing device at its distal end.

In step 210, the sensing device is moved from a first position to a second position. In one embodiment, in the first position the sensing device substantially forms a continuum along the longitudinal axis of the tube and in the second position the sensing device does not form such a continuum. In other embodiments, other movements may be performed, to and from other positions.

In step 220, an in-vivo procedure may be performed. For example, the movement of the sensing device may un-block working channels in the tube, allowing their use for procedures.

Other steps and other series of steps may be used.

It will be appreciated by persons skilled in the art that systems and methods that suitably combine any of the above described embodiments, are also included in the present invention. Furthermore, it will be appreciated that although embodiments of the invention were described relating to an image sensor, other suitable in vivo sensing devices may be used such as temperature sensing devices, pH sensors, pressure sensors, ultrasonic imagers, etc. It will be appreciated that the present invention is not limited to what has been particularly shown and described hereinabove. Rather the scope of the present invention is defined only by the claims which follow.

What is claimed is:

1. A system far maneuvering a device in vivo, the system comprising:
    a tube having a longitudinal axis, a distal end and a proximal end; and
    an in vivo sensing device configured to be connected at a plurality of changeable positions to the distal end of the tube.

2. The system according to claim 1 wherein the in vivo sensing device is an image sensor.

3. The system according to claim 1 wherein the in vivo sensing device comprises two image sensors.

4. The system according to claim 1 wherein the in vivo, sensing device comprises at least two optical paths.

5. The system according to claim 1 wherein the in vivo sensing device comprises at least one illumination source, at least one image sensor and at least one transmitter.

6. The system according to claim 5 wherein the transmitter is a wireless transmitter.

7. The system according to claim 1 wherein the in vivo sensing device comprises an optical window.

8. The system according to claim 5 comprising an external receiving unit.

9. The system according to claim 1 wherein the in vivo sensing device is changeably connected to the distal end of the tube in at least one first mode and in at least one second mode,
    in which at least one first mode the sensing device is connected to the distal end of the tube, to form a continuum along the longitudinal axis of the tube and
    in which at least one second mode the sensing device is connected to the distal end of the tube so as not to form a continuum along the longitudinal axis of the tube.

10. The system according to claim 9 wherein in at least one second mode the sensing device is connected to the distal end of the tube so as to be positioned substantially in parallel to the longitudinal axis of the tube.

11. The system according to claim 1 wherein the tube comprises at least one working channel.

12. The system according to claim 1 wherein the tube comprises a ramp connected to the distal end of the tube.

13. The system according to claim 1 wherein the tube comprises a retractable arm.

14. The system according to claim 1 wherein the in vivo sensing device is coupled to the tube by a hinge.

15. A method for performing in vivo procedures, the method comprising:
    inserting in vivo a tube having:
        a longitudinal axis;
        a distal end;
        and a proximal end; and
        an in vivo sensing device changeably connected to the distal end of the tube wherein the in vivo sensing device is changeably connected to the distal end of the tube in at least one first mode and in at least one second mode, in which at least one first mode the sensing device is connected to the distal end of the tube to form a continuum along the longitudinal axis of the tube and in which at least one second mode the sensing device is connected to the distal end of the tube so as not to form a continuum along the longitudinal axis of the tube;

changing the connection of the sensing device from a first mode to a second mode; and performing an in vivo procedure.

16. A device for maneuvering a device in vivo, the device comprising:
    a tube having a distal end and a proximal end; and
    an in vivo sensing device configured to be connected at a plurality of changeable positions to the distal end of the tube, wherein the sensing device may be moved from a first position to a second position.

17. The device according to claim 16 wherein the in vivo sensing device includes an image sensor.

18. The device according to claim 16 wherein the first position is substantially within the axial profile of the tube.

19. The device according to claim 16 wherein the second position is at least partially outside the axial profile of the tube.

20. The device according to claim 16 wherein in the first position sensing device substantially forms a continuum with the longitudinal axis of the tube.

21. The device according to claim 16 wherein in the second position the in vivo sensing device is positioned alongside the tube.

22. The device according to claim 16 wherein the in vivo sensing device comprises a radio transmitter.

23. The device according to claim 16 wherein the tube comprises at least one working channel.

24. The device according to claim 16 comprising a wire connecting the sensing device and the tube.

25. The device according to claim 16 comprising an elastic cord connecting the sensing device and the tube.

26. The device according to claim 16 wherein the distal end of the tube comprises a hinge.

27. The device according to claim 16 wherein the tube comprises a ramp connected to the distal end of the tube.

28. A device for maneuvering an imaging device in vivo, the device comprising:
    a tube having a distal end and a proximal end; and
    an in vivo imaging device configured to be connected at a plurality of changeable positions to the distal end of the tube, wherein the imaging device may be moved from a first position to a second position.

29. A device for maneuvering a sensing device in vivo, the device comprising:
    a tube having a distal end and a proximal end; and
    a sensing device configured to be connected at a plurality of changeable positions to the distal end of the tube, wherein the sensing device may be moved from a first position to a second position at least partially outside the axial profile of the tube.

30. A device for maneuvering a sensing device in vivo, the device comprising:
    a tube means for inserting an in vivo sensing device means, the tube means having a distal end and a proximal end; and
    a sensing device means for providing images, the sensing device means configured to be connected at a plurality of changeable positions to the distal end of the tube means, wherein the sensing device may be moved from a first position to a second position.

31. A device for maneuvering a sensing device in vivo, the device comprising:
    a tube means for inserting an in vivo sensing device means, the tube means having a distal end and a proximal end; and
    a sensing device means for providing in-vivo sensing, the sensing device means configured to be connected at a plurality of changeable positions to the distal end of the tube means, wherein the sensing device means may be moved from a first position wherein the sensing device means substantially forms a continuum with the longitudinal axis of the tube means to a second position wherein the sensing device does not form a continuum with the longitudinal axis of the tube means.

32. A method for performing in vivo procedures, the method comprising:
    inserting into a body a device comprising:
        a tube having a distal end and a proximal end; and
        an in vivo sensing device configured to be connected at a plurality of changeable positions to the distal end of the tube,
    wherein the sensing device may be moved from a first position to a second position; and
    changing the position of the sensing device from a first position to a second position.

33. The method of claim 32, comprising performing an in vivo procedure.

34. The method of claim 32, comprising moving the sensing device from a position where the sensing device substantially forms a continuum with the longitudinal axis of the tube to a position where the sensing device does not substantially form a continuum with the longitudinal axis of the tube.

35. The method of claim 32 wherein in the second position the in vivo sensing device is positioned alongside the tube.

36. A method for performing in vivo procedures, the method comprising:
    inserting into a body a device comprising:
        a tube having a working channel, a distal end and a proximal end; and
        an in vivo imaging device configured to be connected at a plurality of changeable positions to the distal end of the tube; and
    changing the position of the imaging device from a first position to a position where the imaging device substantially forms a continuum with the longitudinal axis of the tube to a position where the imaging device does not substantially form a continuum with the longitudinal axis of the tube.

* * * * *